(12) United States Patent  
Arimoto et al.

(10) Patent No.: US 9,176,046 B2
(45) Date of Patent: Nov. 3, 2015

(54) ANALYZING DEVICE

(71) Applicant: HORIBA, Ltd., Kyoto-shi, Kyoto (JP)

(72) Inventors: Kimihiko Arimoto, Kyoto (JP); Daisuke Kitaki, Kyoto (JP); Yutaka Dejima, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 0 days.

(21) Appl. No.: 14/247,015

(22) Filed: Apr. 7, 2014

(65) Prior Publication Data
US 2014/0300894 A1 Oct. 9, 2014

(30) Foreign Application Priority Data

Apr. 8, 2013 (JP) .................................. 2013-080230

(51) Int. Cl.
*G01N 1/00* (2006.01)
*G01N 21/03* (2006.01)
(52) U.S. Cl.
CPC .... *G01N 21/0303* (2013.01); *G01N 2021/0375* (2013.01)
(58) Field of Classification Search
CPC .............. G01N 3/08; C12Q 1/02; C12Q 3/00; C12Q 1/6816; C12Q 2565/629; C12Q 1/00; C12Q 1/28; C12Q 1/68; G02B 26/0825; G02B 26/0875; G02B 27/28; G02B 3/14; G02B 6/245; G02B 6/25; G02B 6/3616
See application file for complete search history.

(56) References Cited

U.S. PATENT DOCUMENTS

| | | | | |
|---|---|---|---|---|
| 3,523,737 A | * | 8/1970 | Wood et al. | 356/409 |
| 4,446,106 A | * | 5/1984 | Nelson et al. | 422/72 |
| 4,549,809 A | * | 10/1985 | Minekane et al. | 356/436 |
| 4,550,084 A | * | 10/1985 | Nelson et al. | 436/45 |
| 4,695,164 A | * | 9/1987 | Zivitz et al. | 356/427 |
| 6,047,082 A | * | 4/2000 | Rhody et al. | 382/141 |
| 2009/0104710 A1 | * | 4/2009 | Zhou et al. | 436/164 |
| 2014/0072997 A1 | * | 3/2014 | Yamamoto et al. | 435/30 |

FOREIGN PATENT DOCUMENTS

JP  2007155494 A  6/2007

* cited by examiner

*Primary Examiner* — Michael P Stafira
(74) *Attorney, Agent, or Firm* — Alleman Hall McCoy Russell & Tuttle LLP

(57) ABSTRACT

This invention is to distinguish a position of a measurement cell without using a position sensor that is an electric component, and comprises a cell switching mechanism that switches a measurement position where the measurement cell is located on an optical path and an evacuating position where the measurement cell is evacuated from the optical path so as to make a first moving speed from the measurement position to the evacuating position different from a second moving speed from the evacuating position to the measurement position, and a distinguishing mechanism that detects speed information relating to the first moving speed and the second moving speed by the use of a measurement light and distinguishes the measurement position and the evacuating position.

4 Claims, 6 Drawing Sheets (1) MEASUREMENT POSITION P  (2) EVACUATING POSITION Q (1) MEASUREMENT POSITION P (2) EVACUATING POSITION Q

ANALYZING DEVICE

FIELD OF THE ART

This invention relates to an analyzing device.

BACKGROUND ART

As a conventional analyzing device, for example, as shown in the patent document 1, there is a spectroscopic analyzing device that measures concentrations of a chemical solution used for semiconductor manufacturing device such as a semiconductor cleaning device. The spectroscopic analyzing device comprises a measurement cell that houses a chemical solution, a light irradiating part that irradiates a measurement light on the measurement cell, a light detecting part that detects a transmitted light having passed through the measurement cell and a calculating device that calculates a concentration of the chemical solution based on a light intensity signal obtained by the light detecting part. The spectroscopic analyzing device is configured to conduct a correction on the light irradiating part or the light detecting part by periodically switching a measurement position where the measurement cell is located on an optical path and an evacuating position where the measurement cell is not located on the optical path by relatively moving the optical path formed between the light irradiating part and the light detecting part and the measurement cell.

In order to relatively move the optical path and the measurement cell, the spectroscopic analyzing device comprises a switching mechanism for switching the measurement cell between the measurement position and the evacuating position. In addition, a position sensor is provided as an electrical component using magnetism or light in order to detect the position of the measurement cell switched by the switching mechanism.

However, in the case that the measurement cell is arranged inside of, for example, the semiconductor manufacturing device, the inside environment is a chemical solution atmosphere and some of the chemical solutions are flammable. As mentioned above, in the case that the measurement cell is arranged in a flammable gas atmosphere, it is generally advisable to avoid using an electrical component in the gas atmosphere as much as possible. As a result of this, usage environment is limited such that the position sensor, which is the electrical component that is used to detect the position of the measurement cell, cannot be used in the flammable gas atmosphere.

Meanwhile, in the case that no position sensor is arranged, the position of the measurement cell cannot be detected in controlling the switching mechanism so that it is not possible for the analyzing device to detect whether the measurement cell is normally switched by the switching mechanism.

PRIOR ART DOCUMENT

Patent Document

Patent document 1: Japanese unexamined patent application publication No. 2007-155494

DISCLOSURE OF THE INVENTION

Problems to be Solved by the Invention

A main object of this invention is to distinguish a position of a measurement cell without using a position sensor that is an electric component.

Means to Solve the Problems

More specifically, an analyzing device in accordance with this invention is characterized by comprising a cell switching mechanism that switches a measurement position where a measurement cell that houses a measurement specimen is located on an optical path and an evacuating position where the measurement cell is evacuated from the optical path and that is configured to make a first moving speed from the measurement position to the evacuating position different from a second moving speed from the evacuating position to the measurement position, and a distinguishing mechanism that detects speed information relating to the first moving speed and the second moving speed by the use of the light used for measuring the measurement specimen and that distinguishes the measurement position and the evacuating position.

In accordance with this arrangement, since the first moving speed from the measurement position to the evacuating position is made to be different from the second moving speed from the evacuating position to the measurement position and the position of the measurement cell is distinguished by detecting the speed information relating to the first moving speed and the second moving speed by the use of the light, it is possible to omit a position sensor that is an electrical component. With this arrangement, it is possible to use the measurement cell and the cell switching mechanism even in the flammable gas atmosphere. In addition, since the distinguishing mechanism detects the speed information by the use of the light used for measuring the measurement specimen, there is no need of another detecting optical system to detect the speed information and it is possible to distinguish the measurement position and the evacuating position by the use of the measurement optical system used for measurement. With this arrangement, the structure of the analyzing device can be simplified and downsized.

That the first moving speed is different from the second moving speed includes not only that a magnitude of the moving speed in moving with a continuous speed differs from each other but also that a time change, namely a waveform plotted with a time as the x-axis and a speed as the y-axis, differs from each other.

In addition, in the evacuating position, another measurement cell other than the above-mentioned measurement cell, a reference cell for correction or an optical element such as an optical filter for correction, may be located on the optical path.

With this arrangement, it is possible to distinguish the measurement cell, the reference cell or the optical element locating on the optical path without using a position sensor as being an electric component.

For example, in the case that the cell switching mechanism uses a pneumatic actuator such as an air cylinder, the first moving speed and the second moving speed fluctuate due to a supplied air pressure to the pneumatic actuator.

With this arrangement, it is preferable that the measurement position and the evacuating position are distinguished by detecting a ratio between the speed information relating to the first moving speed and the speed information relating to the second moving speed.

In accordance with this arrangement, since the ratio of the speed information is detected, it is possible to distinguish the measurement position and the evacuating position irrespective of a change of the moving speed in association with a fluctuation of the supplied air pressure.

It is preferable that an optical path blocking member that blocks the optical path in association with a movement between the measurement position and the evacuating position due to the cell switching mechanism is provided, and the distinguishing mechanism detects a time period while the optical path is blocked by the optical path blocking member as the speed information and distinguishes the measurement position and the evacuating position.

With this arrangement, since the analyzing device detects the state wherein the light is blocked by the light blocking member, it is possible to detect the speed information with accuracy. As a result of this, it is possible to distinguish the measurement position and the evacuating position furthermore accurately.

It is preferable that the cell switching mechanism comprises a pneumatic actuator that has a first supply port that supplies air for moving the measurement cell from the measurement position to the evacuating position and a second supply port that supplies air for moving the measurement cell from the evacuating position to the measurement position and a flow channel resistor that is arranged on the first supply port, a first supply pipe that is connected to the first supply port, the second supply port, or a second supply pipe that is connected to the second supply port, and that makes a flow rate of the air supplied from the first supply port different from a flow rate of the air supplied from the second supply port.

With this arrangement, the first moving speed and the second moving speed due to the cell switching mechanism can be determined by a physical constituting element. In addition, in the case that connection of the first supply pipe and the second supply pipe to the first supply port and the second supply port is incorrect, since the speed information relating to the detected first moving speed and the detected second moving speed is detected conversely to the speed information relating to the first moving speed and the second moving speed in the case that the connection is correct, it is possible for the analyzing device to automatically distinguish the incorrect connection.

Effect of the Invention

In accordance with this invention having the above-mentioned arrangement, since the first moving speed from the measurement position to the evacuating position is made to be different from the second moving speed from the evacuating position to the measurement position and the position of the measurement cell is distinguished by detecting the speed information relating to the first moving speed and the second moving speed by the use of the light, it is possible to omit a position sensor that is an electrical component.

BEST MODES OF EMBODYING THE INVENTION

An analyzing device in accordance with this invention will be explained with reference to drawings.

The analyzing device 100 of this embodiment is used in a state of being incorporated into, for example, a semiconductor manufacturing line and is an absorption spectrophotometer that measures concentrations of a chemical solution used in a process of cleaning in, for example, the semiconductor manufacturing line. The chemical solution is SC-1 (ammonia hydrogen peroxide aqueous solution), SC-2 (hydrochloric hydrogen peroxide aqueous solution), SPM (sulfuric acid hydrogen peroxide aqueous solution), FPM (hydrofluoric acid hydrogen peroxide aqueous solution), BHF (buffered hydrofluoric acid aqueous solution) or the like.

Figure 1:
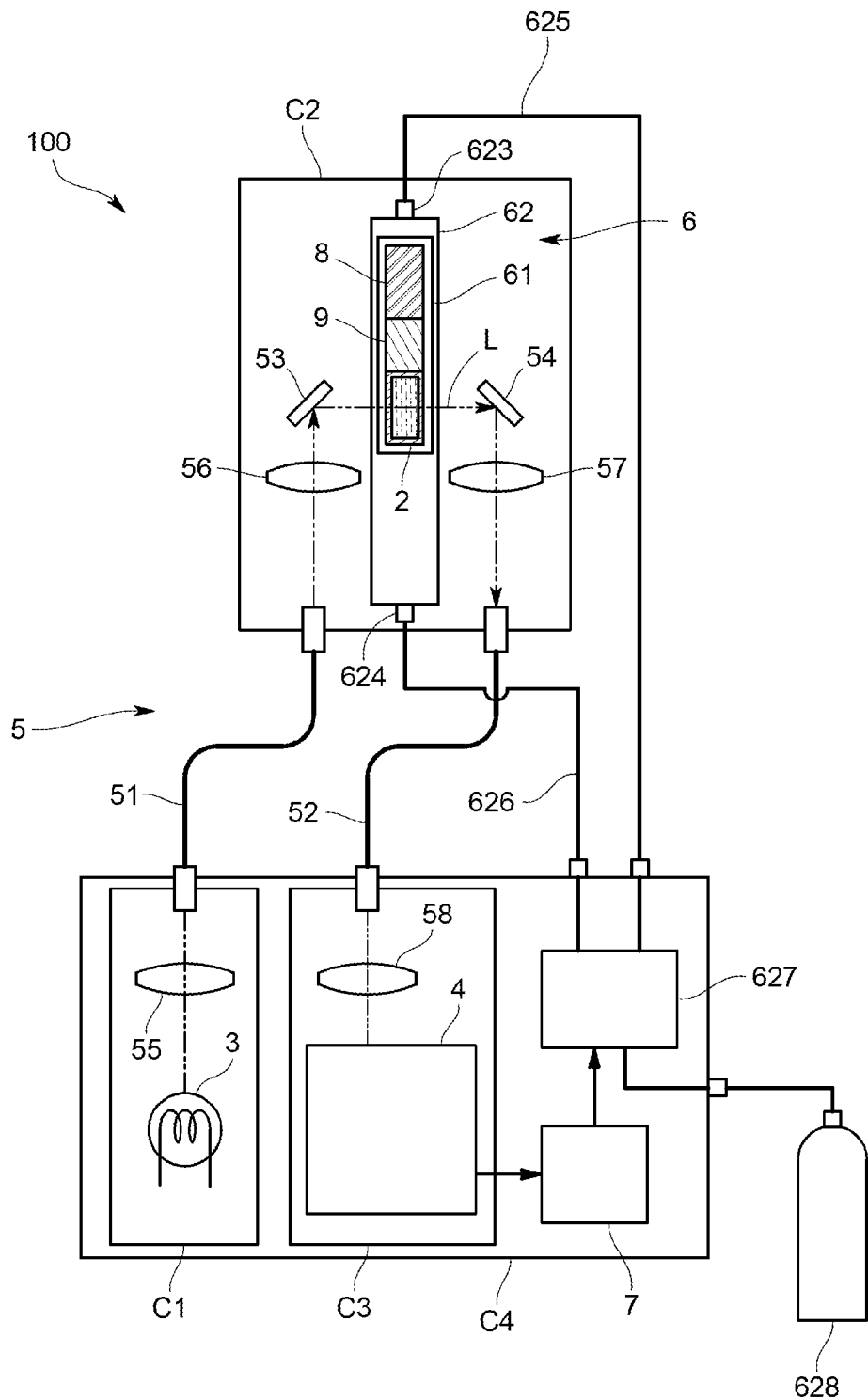
FIG. 1 is a pattern diagram showing an arrangement of an optical analyzing device of this embodiment.

Concretely, the analyzing device 100 comprises, as shown in FIG. 1, a measurement cell 2 where a liquid sample such as a chemical solution is housed, a light source 3 such as a halogen lamp to irradiate the light on the measurement cell 2, a light detecting part 4 to detect the light that has passed through the measurement cell 2 and a light transmitting device 5 that guides the light from the light source 3 to the measurement cell 2 and that guides the light having passed through the measurement cell 2 to the light detecting part 3.

The measurement cell 2 is a flow cell that is arranged on a circulation path formed by a chemical solution pipe connected to a chemical solution tank of, for example, a semiconductor cleaning device. The measurement cell 2 may be an in-line flow cell that is directly incorporated into a pipe of the semiconductor cleaning device.

The light detecting part 4 is a spectroscope that disperses the light having passed through the measurement cell 2 and detects its optical spectrum (a light intensity at each wavelength). The spectroscopic spectral data obtained by the spectroscope 4 is output to an arithmetic unit, not shown in drawings, and calculates an absorbance spectrum of the chemical solution based on the spectroscopic spectra obtained by the spectroscope 4 and the spectroscopic spectra obtained by a correction liquid whose absorbance is known, and calculates a concentration of a component contained in the liquid sample by the use of the absorbance spectrum.

The light transmitting device 5 comprises a first optical fiber 51 that is arranged between the light source 3 and the measurement cell 2 and that leads the light from the light source 3 to the measurement cell 2, a second optical fiber 52 that is arranged between the measurement cell 2 and the light detecting part 4 and that leads the light having passed the measurement cell 2 to the light detecting part 4, a first reflecting member 53 such as a reflecting mirror arranged between the first optical fiber 51 and the measurement cell 2, and a second reflecting member 54 such as a reflecting mirror arranged between the measurement cell 2 and the second optical fiber 52.

In addition, a condensing lens 55 to condense the light from the light source 3 on a light introducing end surface of the first optical fiber 51 is arranged between the light introducing end surface and the light source 3. A condensing lens 56 to condense the light coming out from a light leading out end surface of the first optical fiber 51 on the measurement cell 2 is arranged between the light leading out end surface and the first reflecting member 53.

Furthermore, a condensing lens 57 to condense the light from the second reflecting member 54 on a light introducing end surface of the second optical fiber 52 is arranged between the light introducing end surface and the second reflecting member 54. A condensing lens 58 to condense the light coming out from a light leading out end surface of the second optical fiber 52 on an incident slit of the spectroscope 4 is arranged between the light leading out end surface of the second optical fiber 52 and the light detecting part 4.

In this embodiment, a light source housing case C1 that houses the light source 3 and a measurement cell housing case C2 that houses the measurement cell 2 are connected by the first optical fiber 51, and the measurement cell housing case C2 and a light detecting part housing case C3 that houses the light detecting part 4 are connected by the second optical fiber 52. A light introducing end part (a part having the light introducing end surface) of the first optical fiber 51 is fixed to a side wall of the light source housing case C1 and a light lead out end part (a part having the light lead out end surface) of the first optical fiber 51 is fixed to a side wall of the measurement cell housing case C2 so that whole of the first optical fiber 51 is fixed. In addition, a light introducing end part (a part having the light introducing end surface) of the second optical fiber 52 is fixed to the side wall of the measurement cell housing case C2 and a light lead out end part (a part having the light lead out end surface) of the second optical fiber 52 is fixed to the light detecting part housing case C3 so that whole of the second optical fiber 52 is fixed. In this embodiment, the light lead out end part of the first optical fiber 51 and the light introducing end part of the second optical fiber 52 are fixed to the identical side wall of the measurement cell housing case C2. This arrangement facilitates maintenance of the measurement cell housing case C2. Furthermore, the condensing lens 55 is housed in the light source housing case C1. The first reflecting member 53, the second reflecting member 54 and the condensing lenses 56, 57 are housed in the measurement cell housing case C2. The condensing lens 58 is housed in the light detecting part housing case C3. The light source housing case C1 and the light detecting part housing case C3 are housed in a single case C4, however, each of the light source housing case C1 and the light detecting part housing case C3 may be a single case respectively. In addition, each of the cases C1~C4 is of a shape covering all surfaces and separated from an outside space, however, it may be of a shape whose one part (for example, one surface) is open.

Figure 2:
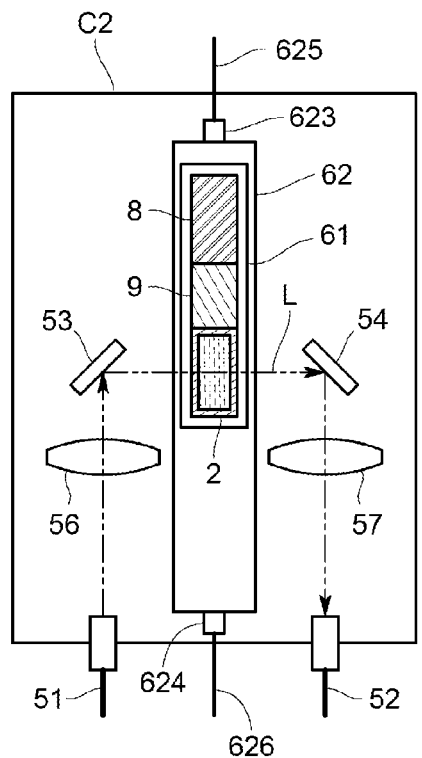
FIG. 2 is a pattern diagram showing a measurement position and an evacuation position of this embodiment.
Figure 2:
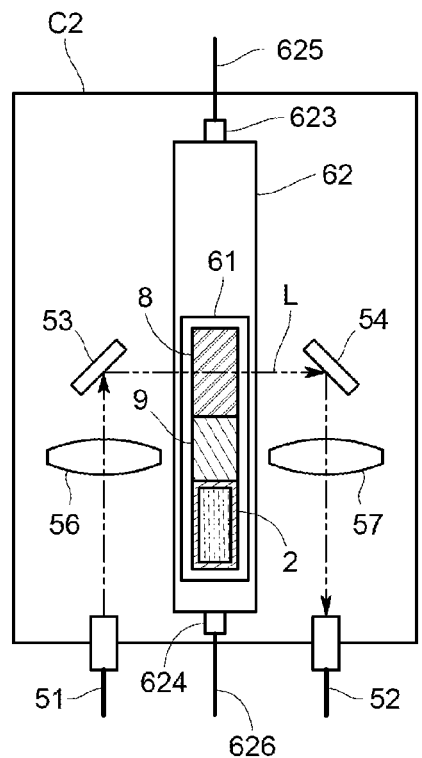

The analyzing device 100 of this embodiment comprises, as shown in FIG. 2, a cell switching mechanism 6 that switches a measurement position (P) (refer to (1)) where the measurement cell 2 that houses a measurement specimen is located on an optical path (L) and an evacuating position (Q) (refer to (2)) where the measurement cell 2 is evacuated from the optical path (L), and a distinguishing mechanism 7 that distinguishes whether the measurement cell 2 is located at the measurement position (P) or the evacuating position (Q).

The measurement position (P) is a position where the optical path (L) formed by the light transmitting device 5 passes through the measurement cell 2. In addition, the evacuating position (Q) is a position where the optical path (L) formed by the light transmitting device 5 passes through an area different from the measurement cell 2. At the evacuating position (Q) of this embodiment, the optical path (L) between the first reflecting member 53 and the second reflecting member 54 passes a filter 8 for correction.

The cell switching mechanism 6 switches the measurement position (P) where the measurement cell 2 is located on the optical path (L) between the first reflecting member 53 and the second reflecting member 54 and the evacuating position (Q) where the measurement cell 2 is evacuated from the optical path (L) between the first reflecting member 53 and the second reflecting member 54 by moving a loading table 61 on which the measurement cell 2 and the filter 8 for correction are loaded.

In addition, the cell switching mechanism 6 is so configured that a first moving speed (v1) to move the measurement cell 2 from the measurement position (P) to the evacuating position (Q) is different from a second moving speed (v2) to move the measurement cell 2 from the evacuating position (Q) to the measurement position (P). In short, it is so configured that a first moving time period while the measurement cell 2 moves from the measurement position (P) to the evacuating position (Q) is different from a second moving time period while the measurement cell 2 moves from the evacuating position (Q) to the measurement position (P).

As a concrete arrangement, the cell switching mechanism 6 is, as shown in FIG. 1 and FIG. 2, arranged inside of the measurement cell housing case C2 and has the loading table 61 on which the measurement cell 2 and the filter 8 for correction are loaded and a moving mechanism 62 that makes the loading table 61 make straight reciprocal movements.

Figure 3:
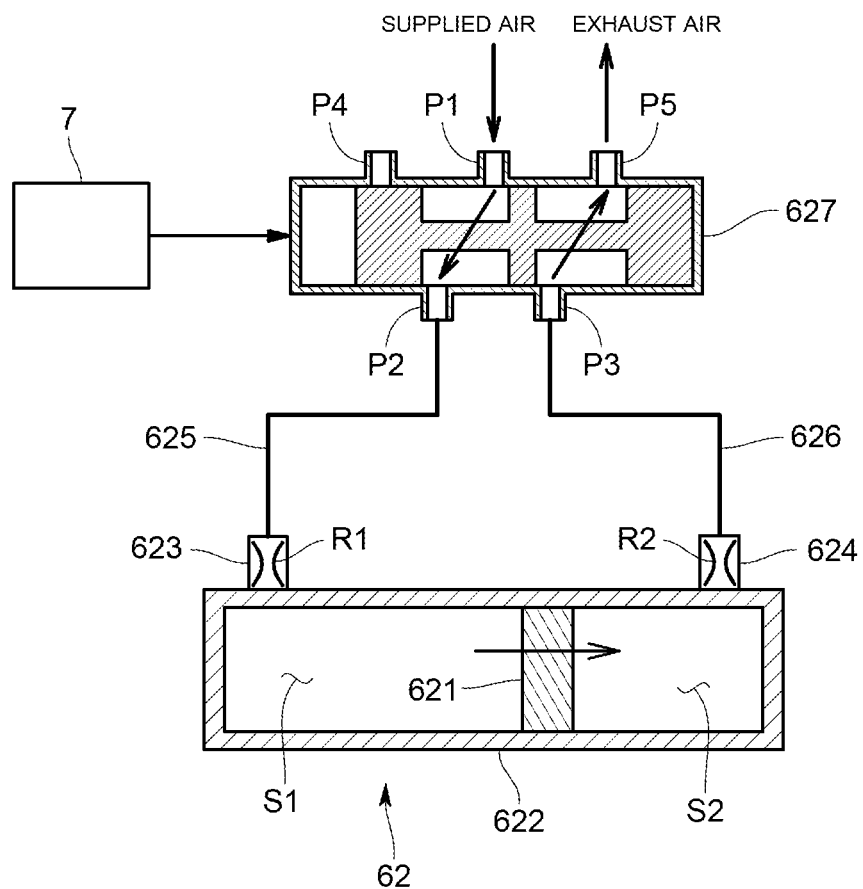
FIG. 3 is a pattern diagram showing an arrangement of a moving mechanism of this embodiment.

The moving mechanism 62 uses an air cylinder as a pneumatic actuator, and comprises, especially as shown in FIG. 3, a piston 621 to which the loading table 61 is connected, a cylinder 622 that has a cylinder chamber housing the piston 621 in a state of being able to make reciprocal movements, a first supply port 623 that is arranged in the cylinder 622 and that supplies compressed air to one space (S1) divided by the piston 621 and a second supply port 624 that is arranged in the cylinder 622 and that supplies compressed air to the other space (S2) divided by the piston 621.

A first supply pipe 625 for supplying the compressed air is connected to the first supply port 623 so that the compressed air for moving the measurement cell 2 from the measurement position (P) to the evacuating position (Q) is supplied. In addition, a second supply pipe 626 for supplying the compressed air is connected to the second supply port 624 so that the compressed air for moving the measurement cell 2 from the evacuating position (Q) to the measurement position (P) is supplied. Furthermore, the first supply pipe 625 and the second supply pipe 626 are connected to a compressed air supply source 628 through a valve mechanism 627 (refer to FIG. 1).

The valve mechanism 627 comprises a four-way solenoid valve as shown in FIG. 3, wherein a first port (P1) is connected to the compressed air source 628, a second port (P2) is connected to the first supply pipe 625, a third port (P3) is connected to the second supply pipe 626, and a fourth port (P4) and a fifth port (P5) are exposed to the atmosphere. With this arrangement, the compressed air is supplied to the first supply port 623 and the second supply port 624 from a single compressed air source 628. This valve mechanism 627 is controlled by the distinguishing mechanism 7, to be described later. Another dedicated control part may be provided in addition to the distinguishing mechanism 7.

In a state that the first port (P1) and the second port (P2) are in communication with each other by moving a valve body, the fourth port (P4) is blocked and the third port (P3) and the fifth port (P5) are in communication with each other. With this arrangement, the compressed air is supplied from the first supply port 623 to the space (S1) so that a piston 621 moves from the measurement position (P) side to the evacuating position (Q) side. In addition, in a state that the first port (P1) and the third port (P3) are in communication with each other by moving the valve body, the fifth port (P5) is blocked and the second port (P2) and the fourth port (P4) are in communication with each other. With this arrangement, the compressed air is supplied from the second supply port 624 to the other space (S2) so that the piston 621 moves from the evacuating position (Q) side to the measurement position (P) side. The valve mechanism 627 is not limited to an arrangement using the four-way solenoid valve, and may be an arrangement using a one-way solenoid valve or a two-way solenoid valve.

For the moving mechanism 62 of this embodiment, a first flow channel resistor (R1) is provided for the first supply port 623, and a second flow channel resistor (R2) whose resistor value is different from that of the first flow channel resistor (R1) is provided for the second supply port 624. In short, it is so configured that a flow rate of the compressed air supplied from the first supply port 623 to the space (S1) differs from a flow rate of the compressed air supplied from the second supply port 624 to the other space (S2). This arrangement makes the first moving speed (v1) to move the measurement cell 2 from the measurement position (P) to the evacuating position (Q) different from the second moving speed (v2) to move the measurement cell 2 from the evacuating position (Q) to the measurement position (P). The first flow rate resistor (R1) and the second flow rate resistor (R2) may be provided for the first supply pipe 625 and the second supply pipe 626 respectively, and may be provided for either one of the first supply pipe 625 and the second supply pipe 626.

For the above-mentioned cell switching mechanism 6, the measurement cell 2 and the filter 8 for correction are movable, and the first optical fiber 51 and the second optical fiber 52 are fixed so as not to move when switching the measurement position (P) and evacuating position (Q). Other elements constituting the light transmitting device 5, namely, condensing lenses 55~58 also are fixed so as not to move when switching the measurement position (P) and the evacuating position (Q).

The distinguishing mechanism 7 detects the speed information relating to the first moving speed (v1) in the case that the measurement cell 2 moves from the measurement position (P) to the evacuating position (Q) and the second moving speed (v2) in the case that the measurement cell 2 moves from the evacuating position (Q) to the measurement position (P) by the use of the light, and distinguishes the measurement position (P) and the evacuating position (Q). The distinguishing mechanism 7 is a dedicated or general-purpose computer comprising, for example, a CPU, a memory, an A/D convertor, a D/A convertor and an input-output interface, not shown in drawings, and produces a function of judging a position of the measurement cell 2 by cooperatively working the CPU and its peripheral devices based on a predetermined program stored in the memory.

The distinguishing mechanism 7 of this embodiment detects the speed information relating to the first moving speed (v1) and the second moving speed (v2) by the use of the measurement light used for measuring a concentration of the measurement specimen housed in the measurement cell 2, concretely by the use of the light source 3 and the light detecting part 4 and distinguishes the measurement position (P) and the evacuating position (Q). In short, the distinguishing mechanism 7 distinguishes the measurement position (P) and the evacuating position (Q) by the use of the light that is irradiated from the light source 3 and that enters the light detecting part 4. The distinguishing mechanism 7 of this embodiment distinguishes the measurement position (P) and the evacuating position (Q) by the use of the light that is irradiated from the light source 3, passes the first optical fiber 51 and the second optical fiber 52 successively and enters the light detecting part 4. Concretely, the distinguishing mechanism 7 obtains a light signal obtained by the light detecting part 4 at a time when the measurement cell 2 is moved and calculates speed information of the first moving speed (v1) and the second moving speed (v2).

Furthermore, the distinguishing mechanism 7 detects a ratio between the speed information relating to the first moving speed (v1) and the speed information relating to the second moving speed (v2) and distinguishes the measurement position (P) and the evacuating position (Q).

Figure 4:
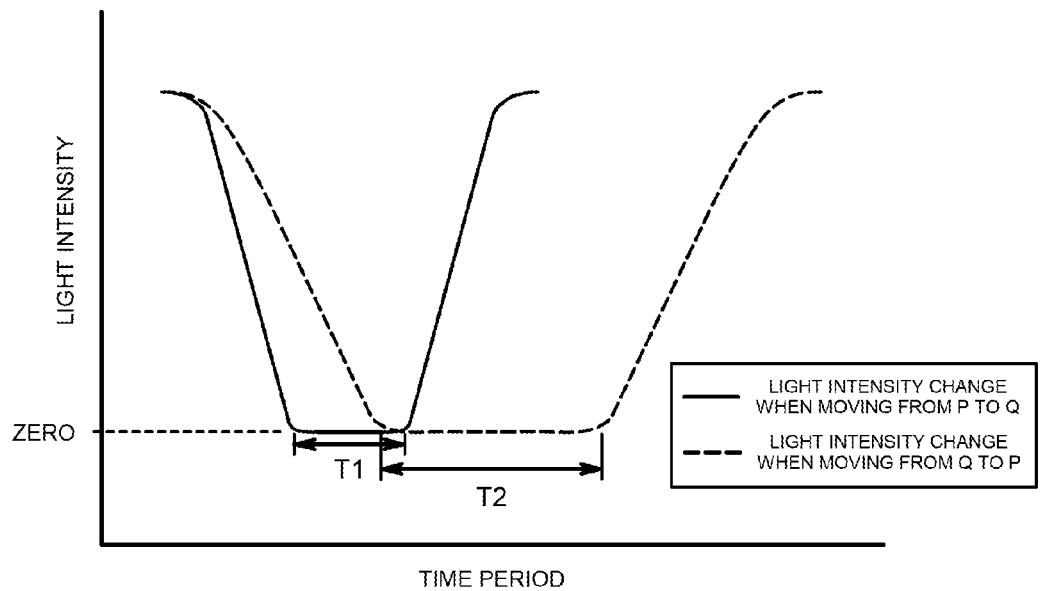
FIG. 4 is a pattern diagram showing a light intensity in association with a movement of the measurement position and the evacuating position of this embodiment.

In this embodiment, as shown in FIG. 1 and FIG. 2, an optical path blocking member 9 that blocks the optical path (L) by moving between the measurement position (P) and the evacuating position (Q) due to the cell switching mechanism 6 is arranged between the measurement cell 2 and the filter 8 for correction, and the distinguishing mechanism 7 detects the time period while the optical path (L) is blocked by the optical path blocking member 9 as the speed information and distinguishes the measurement position (P) and the evacuating position (Q). Concretely, as shown in FIG. 4, in the case that the first moving speed (v1) from the measurement position (P) to the evacuating position (Q) is faster than the second moving speed (v2) from the evacuating position (Q) to the measurement position (P), a zero term (T1) while the light intensity becomes zero or nearly zero by being blocked by the optical path blocking member 9 in the case of moving from the measurement position (P) to the evacuating position (Q) becomes shorter than a zero term (T2) while the light intensity becomes zero or nearly zero by being blocked by the optical path blocking member 9 in the case of moving from the evacuating position (Q) to the measurement position (P). Then, the distinguishing mechanism 7 calculates the zero term (T1) and the zero term (T2) based on the light intensity signal and calculates a ratio (=T2/T1(=v2/v1)) between the zero term (T1) and the zero term (T2) and distinguishes whether the measurement cell 2 is located at the measurement position (P) or the evacuating position (Q) after the measurement cell 2 has moved. In addition, in the case that the light intensity signal obtained by the light detecting part 4 is more than or equal to the predetermined amount, the distinguishing mechanism 7 of this embodiment distinguishes that the movement of the measurement cell 2 is completed and the measurement can be conducted.

Next, one example of an initial movement of the analyzing device 100 having the above-mentioned arrangement will be explained.

First, when the analyzing device 100 is started up, the control device constituting the distinguishing mechanism 7 controls the cell switching mechanism 6 and moves the placing table 61 to an initial position (for example, the measurement position (P)). Next, the placing table 61 is moved from the initial position, the measurement position (P), to the evacuating position (Q) and then the zero term (T1) at this time is calculated. Next, the placing table 61 is moved from the evacuating position (Q) to the measurement position and then the zero term (T2) at this time is calculated. Then, the distinguishing mechanism 7 calculates the ratio between the zero term (T1) and the zero term (T2) and compares the ratio with a previously determined reference value. As a result of the comparison, the distinguishing mechanism 7 determines whether the difference between the ratio (T2/T1) of the zero term (T1) to the zero term (T2) and the reference value falls within the predetermined range or not. If the difference between the ratio (T2/T1) of the zero term (T1) to the zero term (T2) and the reference value is outside of the predetermined range, the distinguishing mechanism 7 distinguishes that there is a problem with the first supply pipe 625 and the second supply pipe 626 to the first supply port 623 and the second supply port 624 of the cell switching mechanism 6 and issues a warning to a user. Meanwhile, if the difference between the ratio (T2/T1) of the zero term (T1) to the zero term (T2) and the reference value falls within the predetermined range, the distinguishing mechanism 7 distinguishes whether the measurement cell 2 is located at the measurement position (P) or at the evacuating position (Q). As a result of the initial movement, the distinguishing mechanism 7 distinguishes the result of the measurement position (P) and then a successive regular measurement of the chemical solution is conducted. The above-mentioned continuous processes may be conducted not only after the initial movement but also periodically prior to or after the correction process, or may be conducted in the case that an error occurs for the position of the measurement cell 2 in the regular measurement of the concentration of the chemical solution.

In accordance with the analyzing device 100 of this embodiment having the above-mentioned arrangement, since the first moving speed (v1) from the measurement position (P) to the evacuating position (Q) is made to be different from the second moving speed (v2) from the evacuating position (Q) to the measurement position (P) and the speed information relating to the first moving speed (v1) and the speed information relating to the second moving speed (v2) are detected by the use of the light and the position of the measurement cell 2 is distinguished, it is possible to omit a position sensor that is an electrical component. With this arrangement, the measurement cell 2 and the cell switching mechanism 6 can be used safely even though they are arranged in a flammable gas atmosphere.

In addition, since the distinguishing mechanism 7 detects the speed information by the use of the measurement light irradiated on the measurement cell 2, there is no need of preparing an additional detecting optical system to detect the speed information and it is possible to distinguish the measurement position (P) and the evacuating position (Q) by the use of the measurement optical system (the light source 3 and the light detecting part 4) to be used for measurement. With this arrangement, it is possible to simplify the arrangement of the analyzing device 100 and to downsize the analyzing device 100.

Furthermore, since the distinguishing mechanism 7 detects the ratio (T2/T1) of the zero term (T1) depending on the first moving speed (v1) to the zero term (T2) depending on the second moving speed (v2) and distinguishes the measurement position (P) and the evacuating position (Q), it is possible to distinguish the measurement position (P) and the evacuating position (Q) accurately irrespective of fluctuation of the moving speed due to the supplied air pressure supplied to an air cylinder.

In addition, since the distinguishing mechanism 7 detects the zero term (T1) and the zero term (T2) while the optical path (L) is blocked between the measurement cell 2 and the filter 8 for correction by the optical path block member 9 as the speed information, and distinguishes the measurement position (P) and the evacuating position (Q), it is possible to detect the speed information accurately. As a result of this, it is possible to distinguish the measurement position (P) and the evacuating position (Q) furthermore accurately.

The present claimed invention is not limited to the above-mentioned embodiment.

Figure 5:
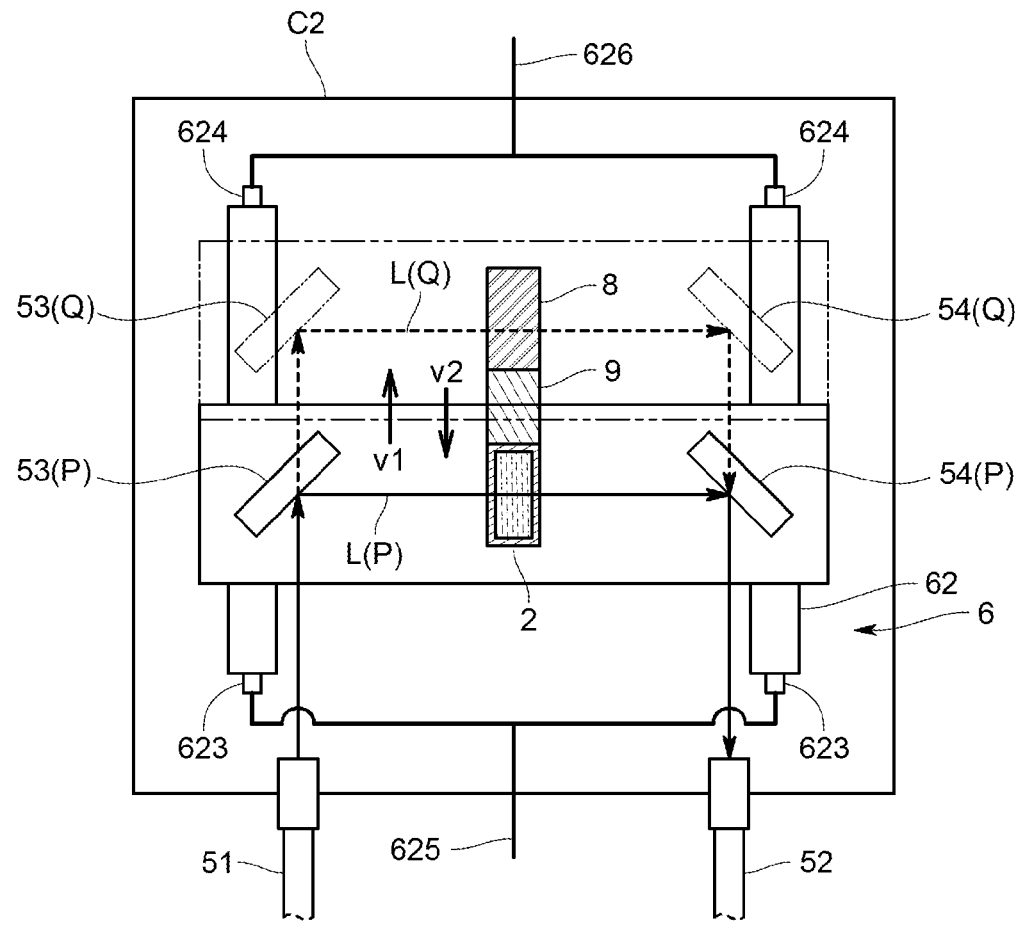
FIG. 5 is a pattern diagram showing an arrangement of an optical analyzing device of a modified embodiment.

For example, the cell switching mechanism 6 switches the measurement position (P) and the evacuating position (Q) by moving the placing table 61 on which the measurement cell 2 is loaded, however, as shown in FIG. 5, the cell switching mechanism 6 may switch the measurement position (P) and the evacuating position (Q) by moving the first reflecting member 53 and the second reflecting member 54. In short, the measurement position (P) and the evacuating position (Q) may be switched only by moving the first reflecting member 53 and the second reflecting member 54. In addition, both of the first reflecting member 53 and the second reflecting member 54 and the measurement cell 2 may be relatively moved. If a pipe connected to the measurement cell 2 is flexible, it is possible to construct the cell switching mechanism 6 like the above-mentioned embodiment. However, if the pipe is not flexible, there would be a problem. As a result of this, it is preferable to move the first reflecting member 53 and the second reflecting member 54.

In addition, in the above-mentioned embodiment, since the chemical solution exists in the atmosphere, from a viewpoint of safety, a pneumatic actuator such as an air cylinder is used, however, an actuator using another operating fluid or a mechanically driven actuator may be used.

Figure 6:
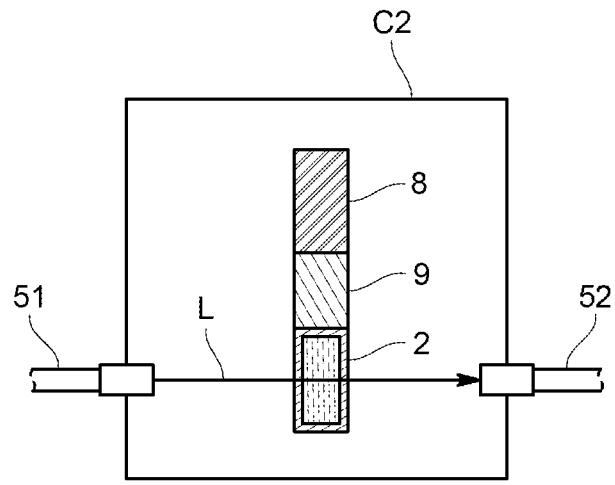
FIG. 6 is a pattern diagram showing an arrangement of an optical analyzing device of a modified embodiment.
Figure 6:
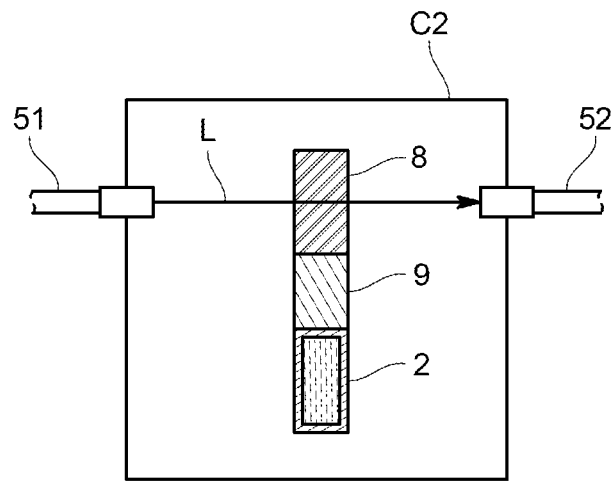

In addition, as shown in FIG. 6, the light from the first optical fiber 51 may be irradiated on the measurement cell 2 without reflecting off the first reflecting member 53 and the second reflecting member 54 and the light having passed the measurement cell 2 may be introduced into the second optical fiber 52. For the arrangement shown in FIG. 6, the measurement cell 2 may be moved without moving the first optical fiber 51 and the second optical fiber 52, or both the first optical fiber 51 and the second optical fiber 52 and the measurement cell 2 may be relatively moved.

Furthermore, the light transmitting device 5 of the above-mentioned embodiment has the first optical fiber 51 and the second optical fiber 52, however, it may have either one of them or may have neither of them. Since the chemical solution gas exists or a space for installation is limited near an area around the measurement cell 2, it is difficult to arrange the light source 3 or the light detecting part 4. As a result of this, it is preferable to arrange the light source 3 and the light detecting part 4 at a position separated from the measurement cell 2 by the use of both the first optical fiber 51 and the second optical fiber 52.

In addition, the filter 8 for correction is arranged on the optical path (L) between the first reflecting member 53 and the second reflecting member 54 in a state that the measurement cell 2 is located at the evacuating position (Q) in the above-mentioned embodiment, however, the optical path (L) may pass through air with an arrangement where nothing is arranged on the optical path (L) between the first reflecting member 53 and the second reflecting member 54. In addition, in a state that the measurement cell 2 is located at the evacuating position (Q), the optical path (L) may pass through another optical cell with an arrangement wherein an optical cell such as another reference cell (for example, a blank cell) or other measurement cell is arranged on the optical path (L) between the first reflecting member 53 and the second reflecting member 54.

In addition, the distinguishing mechanism 7 of the above-mentioned embodiment detects the ratio of the zero term due to the optical path blocking member 9 as the speed information relating to the moving speed, however, the distinguishing mechanism may conduct a judgment by detecting the zero term (T1) and the zero term (T2) due to the optical path blocking member 9. Concretely, it can be conceived that the judgment is conducted by comparing the zero term (T1) with a previously determined first reference value, or by comparing the zero term (T2) with a previously determined second reference value. With this arrangement, it is possible to distinguish the measurement position (P) and the evacuating position (Q) only by a one-way movement without making the cell switching mechanism 6 make reciprocal movements. In addition, the distinguishing mechanism 7 may use a sampling number of the light intensity signal indicating zero or substantial zero generated by the optical path blocking member 9 as the speed information.

Furthermore, in the above-mentioned embodiment, the zero term due to the optical path blocking member 9 is detected as the speed information, however, other light intensity fluctuation such as a moving time period of the light intensity between peaks may be used as the speed information.

In addition, in the above-mentioned embodiment, the position of the measurement cell 2 is switched between two positions, namely the measurement position (P) and the evacuating position (Q), however, the position of the measurement cell 2 may be switched between not only two positions as the measurement position (P) and the evacuating position (Q) but also three or more positions. Also in this case, it can be conceived that each of the moving speeds moving from each position to another position may vary respectively.

In addition, in the above-mentioned embodiment the light source 3 is housed in the light source housing case (C1), the measurement cell 2 is housed in the measurement cell housing case (C2) and the light detecting part 4 is housed in the light detecting part housing case (C3), however, the light source 3 and/or the light detecting part 4 may be housed in the measurement cell housing case (C2).

The distinguishing mechanism 7 in the above-mentioned embodiment distinguishes the position of the measurement cell 2 by the use of the measurement optical system having the light source 3 and the light detecting part 4, however, it may distinguish the speed information relating to the first moving speed (v1) and the second moving speed (v2) by the use of light other than the measurement light and may distinguish the measurement position (P) and the evacuating position (Q). Concretely, the distinguishing mechanism 7 may distinguish the position of the measurement cell by the use of an optical system other than the measurement optical system. For example, a part of the light that is emitted from the light source 3 and that is transmitted by the light transmitting element such as an optical fiber different from the first optical fiber may be used, or the light that is emitted from a light source different from the light source 3 and that is transmitted by the light transmitting element may be used. In addition, the light transmitted by the light transmitting element may be detected by the light detecting part 4, or may be detected by a light detecting part different from the light detecting part 4. With this arrangement, since the first moving speed from the measurement position to the evacuating position is made to be different from the second moving speed from the evacuating position to the measurement position and the position of the measurement cell is distinguished by detecting the speed information relating to the moving speed by the use of the light, it is possible to distinguish the position of the measurement cell with ease.

In addition, it is a matter of course that the present claimed invention is not limited to the above-mentioned embodiment and may be variously modified without departing from the spirit of the invention.

LIST OF REFERENCE CHARACTERS

100 . . . analyzing device
2 . . . measurement cell
3 . . . light source
4 . . . light detecting part
5 . . . light transmitting device
6 . . . cell switching mechanism
7 . . . distinguishing mechanism
8 . . . filter for correction
9 . . . optical path blocking member
L . . . optical path
P . . . measurement position
Q . . . evacuating position
R1 . . . first flow channel resistor
R2 . . . second flow channel resistor
v1 . . . first moving speed
v2 . . . second moving speed
T1 . . . zero term
T2 . . . zero term

The invention claimed is:

1. An analyzing device comprising:
a cell switching mechanism that switches a measurement position where a measurement cell that houses a measurement specimen is located on an optical path and an evacuating position where the measurement cell is evacuated from the optical path and that is configured to make a first moving speed from the measurement position to the evacuating position different from a second moving speed from the evacuating position to the measurement position, and
a distinguishing mechanism that detects first speed information relating to the first moving speed and second speed information relating to the second moving speed by the use of light used for measuring the measurement specimen and that distinguishes the measurement position and the evacuating position using a difference between the first speed information and the second speed information.

2. The analyzing device described in claim 1, wherein
an optical path blocking member that blocks the optical path in association with a movement between the measurement position and the evacuating position due to the cell switching mechanism is provided, and
the distinguishing mechanism detects a time period while the optical path is blocked by the optical path blocking member as the first and second speed information and distinguishes the measurement position and the evacuating position.

3. The analyzing device described in claim 1, wherein
the cell switching mechanism comprises:
a pneumatic actuator that has a first supply port that supplies air for moving the measurement cell from the measurement position to the evacuating position and a second supply port that supplies air for moving the measurement cell from the evacuating position to the measurement position, and
a flow channel resistor that is arranged on the first supply port, a first supply pipe that is connected to the first supply port, the second supply port, or a second supply pipe that is connected to the second supply port, and that makes a flow rate of the air supplied from the first supply port different from a flow rate of the air supplied from the second supply port.

4. An analyzing device comprising:
a cell switching mechanism that switches a measurement position where a measurement cell that houses a measurement specimen is located on an optical path and an evacuating position where the measurement cell is evacuated from the optical path and that is configured to make a first moving speed from the measurement position to the evacuating position different from a second moving speed from the evacuating position to the measurement position, and
a distinguishing mechanism that detects first speed information relating to the first moving speed and second speed information relating to the second moving speed by the use of light and that distinguishes the measurement position and the evacuating position using a difference between the first speed information and the second speed information.

\* \* \* \* \*